United States Patent [19]

Barrett

[11] 4,158,776
[45] Jun. 19, 1979

[54] PATIENT SENSING AND INDICATING ARRANGEMENT FOR A COMPUTED TOMOGRAPHY SYSTEM

[75] Inventor: David M. Barrett, Brookfield, Wis.

[73] Assignee: General Electric Company, Milwaukee, Wis.

[21] Appl. No.: 848,276

[22] Filed: Nov. 3, 1977

[51] Int. Cl.² .............................................. A61B 6/02
[52] U.S. Cl. .............................. 250/445 T; 250/223 R
[58] Field of Search .................... 250/445 T, 560, 223; 33/125 A; 340/678

[56] References Cited

U.S. PATENT DOCUMENTS

| 3,987,902 | 10/1976 | Burgess et al. | 250/223 R |
| 4,005,311 | 1/1977 | Ledley | 250/445 T |

Primary Examiner—Alfred E. Smith
Assistant Examiner—T. N. Grigsby
Attorney, Agent, or Firm—Roger C. Turner

[57] ABSTRACT

An arrangement is provided for sensing and indicating if a cross section of a patient extends beyond an image reconstruction circle during examination. The arrangement is positioned within a generally vertical gantry having a generally cylindrical opening for receiving the patient. The arrangement includes a plurality of light emitting sources disposed within the gantry and which are closely adjacent the reconstruction circle. Each light emitting source projects a light beam along a line which is parallel with the plane of the reconstruction circle and tangent to a cylinder having a diameter and central axis in agreement with the reconstruction circle. The light beams extend substantially across the opening in the gantry and generally inscribe the reconstruction circle. A plurality of photodetectors are disposed within the gantry and aligned to receive each of the light beams. The photodetectors are interconnected to the system by means for indicating an interruption of any of the light beams between any of the sources and detectors.

10 Claims, 5 Drawing Figures

PATIENT SENSING AND INDICATING ARRANGEMENT FOR A COMPUTED TOMOGRAPHY SYSTEM

BACKGROUND OF THE INVENTION

1. FIELD OF THE INVENTION

This invention relates generally to a system for performing computed x-ray tomography and more particularly to an arrangement for precisely sensing and indicating that a patient extends beyond an image reconstruction circle of the system.

2. DESCRIPTION OF THE PRIOR ART

In one method of computed tomography a patient is supported for being translated along a longitudinal axis which is usually horizontally disposed. The axis coincides with the center of rotation of a rotatable gantry which has an x-ray source on one side of the center of rotation and a multiple array of x-ray detectors on the other side. A fan shaped x-ray beam that is thin in the longitudinal direction is projected through the patient as the gantry rotates so that the detectors may develop signals indicative of x-ray transmission characteristics along a plurality of paths through the patient undergoing examination. Analog signals representative of x-ray attenuation by all of the volume elements in a layer of the patient at various rotational angles are then converted to digital signals which are used by a computer to produce signals which may thereafter be used to produce a reconstructed image of the layer. The image is reconstructed by analyzing all of the signals within a central cross-sectional area of the system known as the "reconstruction circle." The analog signals are analyzed and converted based upon all of the x-ray attenuation taking place within the reconstruction circle. If the cross section of the patient is either too large or improperly positioned so that a portion of the patient extends outside of the reconstruction circle, the x-ray attenuation of that portion will be erroneously interpreted. The resulting reconstructed image might not be clear or accurate and could require reexamination, or could even provide misinformation. It is therefore extremely important to know, before the scanning process, whether the patient is properly positioned within the reconstruction circle to alleviate the necessity of reexamination.

One method of sensing an oversized or improperly positioned patient involves the application of mechanical templates and sizing devices physically over and around the patient while the patient is in the staged position. Such devices are awkward to handle, time consuming and are typically removed prior to transalation of the patient into the system. The patient-oversize checks by this method are not always performed closely adjacent to the scan plane. There is time for the patient to shift out of position, between the time of checking and the time of scanning.

A problem associated with the prior art is that the oversized patient check is not done automatically and can be overlooked. Another problem is that there is no opportunity to monitor the patient once in the gantry and between successive scans to insure that the patient remains within the reconstruction circle.

There are situations where the scans will be desired by the physician or radiology technician even though the patient may extend beyond the reconstruction circle. It is important however that these situations always be acknowledged and recorded for proper caution in interpretation of the scans.

Accordingly, one object of this invention is to provide an arrangement to automatically sense and indicate that a patient extends beyond an image reconstruction circle of a computed tomography system.

Another object is to monitor the size and position of the patient over the area to be examined immediately prior to initiating the scanning operation.

Another object is to monitor the size and position of a patient by an arrangement which does not interfere with the patient or the scanning operation and is immediately adjacent to the scan plane of the system.

Another object is to indicate an oversized patient condition on a control panel of the system.

Still another object of this invention is to provide an arrangement to indicate the presence of an oversized patient on an operator's console which requires an operator response, such as, to either abort the scan or override and continue with the examination.

SUMMARY OF THE INVENTION

The invention is directed to an arrangement for sensing and indicating if a cross section of a patient extends beyond an image reconstruction circle during examination by a computed tomography system. The tomography system includes a source of an x-ray beam and a detector disposed on opposite sides of a generally vertical gantry. The terms x-ray and x-ray source are used herein for the sake of brevity and convenience, but these terms should be construed as embracing gamma radiation and the gamma sources and other penetrating radiation and sources as well. The gantry has a generally cylindrical opening for receiving the patient. The patient is supported on a generally horizontal table which is translatable along the longitudinal axis generally centered within the opening of the gantry. The table is displacable for the purpose of disposing longitudinal successive layers of the patient into the path of the x-ray beam.

The sensing and indicating arrangement is generally described as at least one light beam which is generally tangent to the reconstruction circle and which is directed to a corresponding number of photo sensors which signal an interruption of any of the light beams. The arrangement comprises at least one light emitting source disposed within the gantry and which is closely adjacent the reconstruction circle. Each light emitting source projects a light beam along a line which is generally parallel with the plane of the reconstruction circle and generally tangent to a cylinder having a diameter and central axis in agreement with the reconstruction circle. A corresponding number of photo detectors are each disposed within the gantry and aligned to receive each of the light beams. The photosensors are interconnected to the system by means for indicating an interruption of any of the light beams between any of the sources and the detectors.

BRIEF DESCRIPTION OF THE DRAWINGS

While the novel features of the invention are set forth with particularity in the appended claims, the invention will be better understood along with other features thereof from the following detailed description taken in conjunction with the drawings in which:

DESCRIPTION OF THE PREFERRED EMBODIMENT

Figure 2:
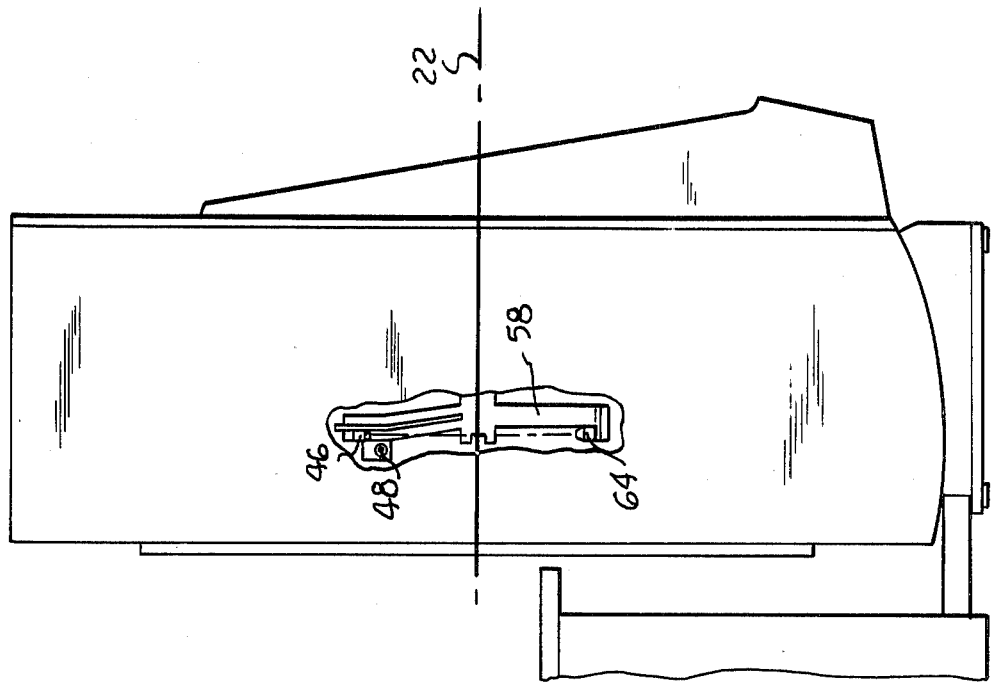
FIG. 2 is a side elevation view of the system shown in FIG. 1 having a cutaway portion revealing the arrangement of the invention.
Figure 1:
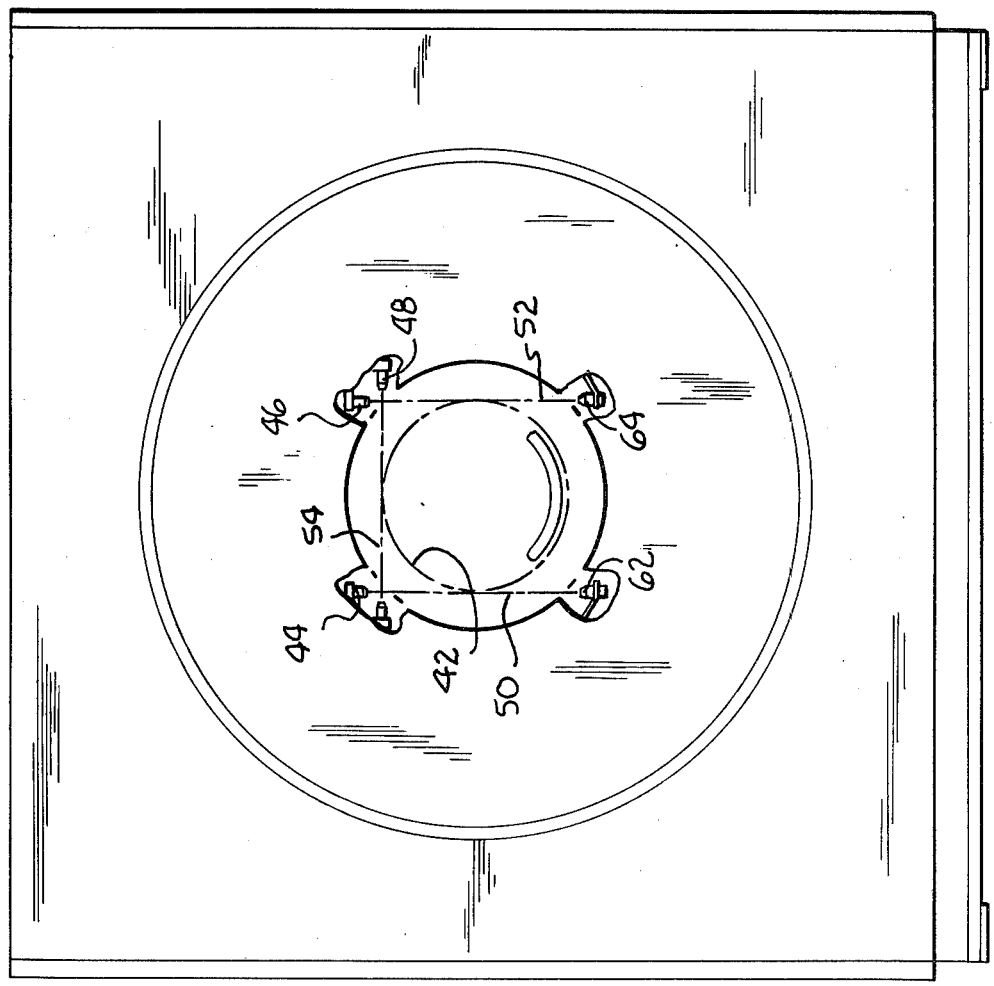
FIG. 1 is a front elevation view of a gantry of a computed tomography system having a cutaway portion revealing the arrangement of this invention.

Referring first to FIGS. 1 and 2 there is shown a portion of a computed tomography system 10. A table for supporting a patient undergoing tomography examination is generally designated by referenced numeral 12. The table has a top 14 on which a patient may be supported in a recumbent position. Top 14 is translatable in the longitudinal direction so that it extends in cantilever fashion from table 12 for the purpose of disposing successive longitudinal layers of a patient's body in the path of a scanning x-ray beam. The mechanism for advancing and retracting the patient longitudinally is within the housing of table 12 and is not shown in detail since it forms no part of the present invention.

X-ray scanning and obtaining x-ray attenuation data on a multitude of small volume elements in the patient is carried out with components of a gantry which is generally designated by the referenced numeral 16. Gantry 16 is generally vertical having a cylindrical opening 18 for receiving the patient for examination. The gantry 16 includes a base 20 about which the components of the gantry can be tilted about a transverse axis and rotated about a central longitudinal axis 22.

Figure 4:
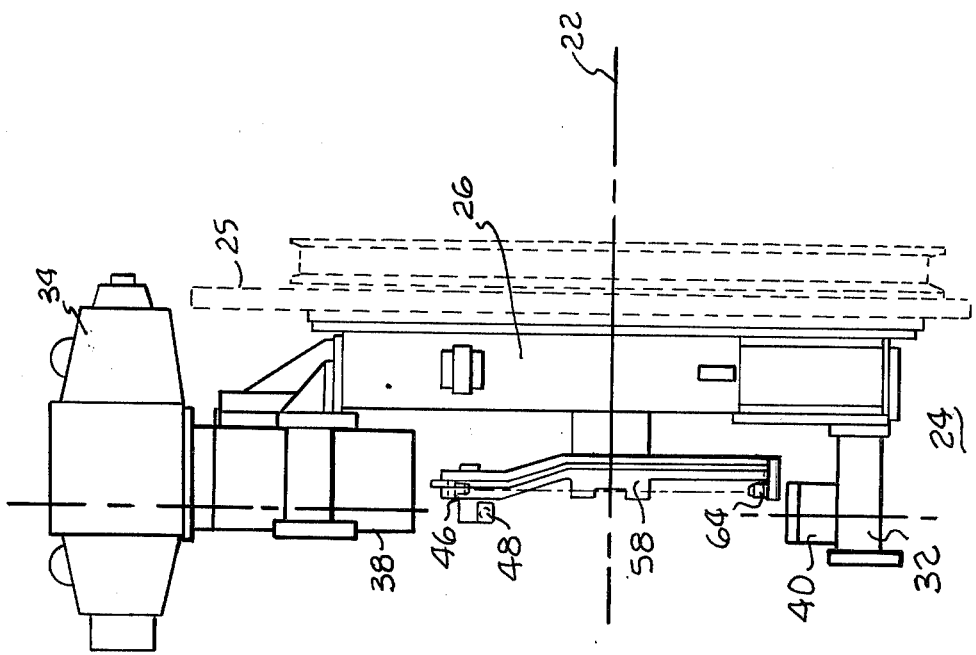
FIG. 4 is a side elevation view of the structure shown in FIG. 3.
Figure 3:
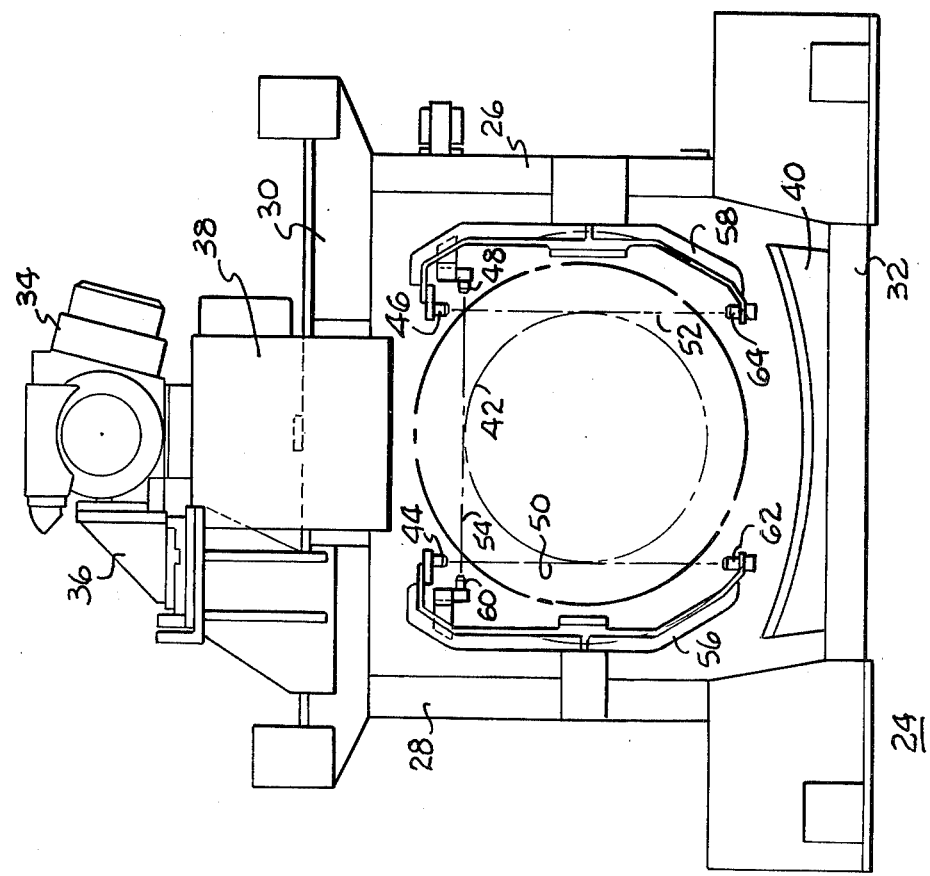
FIG. 3 is a front elevation view of a rotatable base structure of the gantry for supporting the arrangement of the invention.

Basic elements of the gantry 16 are shown in FIGS. 3 and 4 attached to rotatable structure 24. Rotatable structure 24 includes bearing structure 25 for rotation thereon about longitudinal axis 22. In general terms, rotatable structure 24 has a frame comprised of side members 26 and 28, a top cross member 30 and a bottom cross member 32. An x-ray source is mounted to cross member 30 by means of a bracket assembly 36 and positioned so that the central ray of the x-ray beam eminating from the x-ray source passes through the longitudinal axis 22. Mounted to the output side of x-ray source 34 is a collimator device 38 which in this particular design collimates the x-ray beam into a thin fan-shaped beam which originates from a substantially point source on the target of an x-ray tube in source 34. In a commercial embodiment, by way of example, the longitudinal thickness of the x-ray beam is about 1 centimeter and a slice or layer of corresponding thickness in the patient is penetrated by the beam for each scan. An x-ray detector and data acquisition assembly 40 is mounted to bottom cross member 32 and is aligned with collimator 38. The detector portion has a curved x-ray input window behind which there is an array of adjacent detector cells, which are not visible. Each cell produces output signals corresponding with the intensity of the plurality of rays that radiate from the x-ray source and penetrate continuous series of volume elements of a patient layer that is disposed along the longitudinal axis during x-ray examination of the patient. A suitable detector is shown in U.S. Pat. No. 4,031,396 by Whetten et al and assigned to the assignee of this application. Other detector forms are known to those skilled in the art. The descreet plurality of analog signals representative of x-ray attenuation by small volume elements in the patient are processed in a data acquisition system after which the analog signals are converted to digital signals which are used by a computer, not shown, to execute the image reconstruction algorithm. The signals and reconstruction algorithm are computed based upon all of the x-ray attenuation taking place within a central area shown as a dashed line and known as the reconstruction circle 42. Reconstruction circle 42 is concentric with the central axis of rotation of gantry 16 which is also longitudinal axis 22. The reconstruction circle of this particular embodiment has a diameter of 42 centimeters. The above described computed tomography system is generally known in the art.

As previously discussed, it is important that the patient be centered within the reconstruction circle during scanning by the system. A suitable arrangement for facilitating central alignment of the patient in a staged position is described in U.S. Pat. No. 4,117,337, entitled "PATIENT POSITIONING INDICATION ARRANGEMENT FOR A COMPUTED TOMOGRAPHY SYSTEM" and filed concurrently herewith in the name of P. Staats and assigned to the same assignee as this application. However, even though a patient may be centrally aligned with the reconstruction circle 42 at a staged position, the patient may shift out of position or be too large and extend beyond the reconstruction circle. In order to precisely indicate if a portion of a patient extends beyond the reconstruction circle a sensing arrangement is provided and is a principle feature of this invention.

The arrangement is characterized by a set of sources and sensors, such as a photo cell system as described below, inscribing the reconstruction circle 42. Any energy source which can be directed and sensed, such as electromagnetic, infra red and other portions of the energy spectrum could be provided to inscribe the desired area, and the energy beam sources are not limited to light sources. The arrangement of this preferred embodiment comprises light emitting sources 44, 46 and 48 projecting light beams 50, 52 and 54. The light sources are mounted on supporting arms 56 and 58 so that each light beam is projected along a line which is generally parallel to the plane of reconstruction circle 42 and generally tangent to a cylinder in space having a diameter and central axis 22 in agreement with the reconstruction circle. In this preferred embodiment, light source 48 is positioned by the supporting arm 58 so as to project light beam 54 generally horizontally directed substantially across opening 18 and tangent to reconstruction circle 42. Light sources 44 and 46 are positioned by support arms 56 and 58 so as to project light beams 50 and 52 generally vertically directed substantially across opening 18 but which are 2.5 centimeters behind the plane of reconstruction circle 42 so as not to interfere with the x-ray beam eminating from collimator 38. A bottom horizontal beam is not necessary since the patient is confined by supporting table top 14 and thereby the lower sector is always within the reconstruction circle. The three light beams 50, 52 and 54 generally define three sides of a square having sides of 42 centimeters and inscribe the 42 centimeter reconstruction circle. When rotatable structure 24 is rotated with gantry 16, the light beams define a 42 centimeter circle. A suitable light emitting source is known as the Skan-a-matic L 130 which is a #12 bi-pin 6.3 volt and 0.18 amp. lamp.

Corresponding detectors 60, 62 and 64 are also mounted to support arms 56 and 58 and are aligned to receive each of said light beams at the opposite side of opening 18. A suitable photodetector is commercially available as the Skan-a-matic P 130 having a rise and fall time of 3 microseconds and a forward current of 20 milliamps. The light emitting sources 44, 46 and 48 and photodetectors 60, 62 and 64 are electrically wired in parallel so that an interruption of any of light beams 50, 52 or 54 would produce a signal indication.

The three mutually perpendicular light beams 50, 52 and 54 inscribing the reconstruction circle 42 and substantially in the same plane as the reconstruction circle is the preferred embodiment of the arrangement. The location of the light beams within the gantry also serve to automatically reduce the sensing height correspondingly with the reduced height of the reconstruction circle when the gantry is in the tilted position. However, a variety of positions and quantity of sources and detectors could alternatively be arranged to inscribe the reconstruction circle. A single light beam (as 52), which is tangent to or closely adjacent to one point of the reconstruction circle 42 could be rotated to make a perimeter check of the entire reconstruction circle.

The most likely locations for a patient to extend beyond the reconstruction circle is at either side. The recumbent body tends to be horizontally oval-shaped in cross section and also the arms can sometimes be extended to the side and out of the circle. As an alternative arrangement, two vertically tangent beams (such as 50 and 52) and which would not even need to rotate, would provide a sensing arrangement with some degree of reliability.

Another set of light beams could alternatively be arranged forward of gantry 16 and in the path of the translatable tabletop 14 along longitudinal axis 22. The forwardly arranged beams would be tangent to a cylinder having a diameter and central axis in agreement with the reconstruction circle 42 and thereby sense if the patient extended beyond the circle as the patient was translated adjacently beside the beams and into the gantry.

Figure 5:
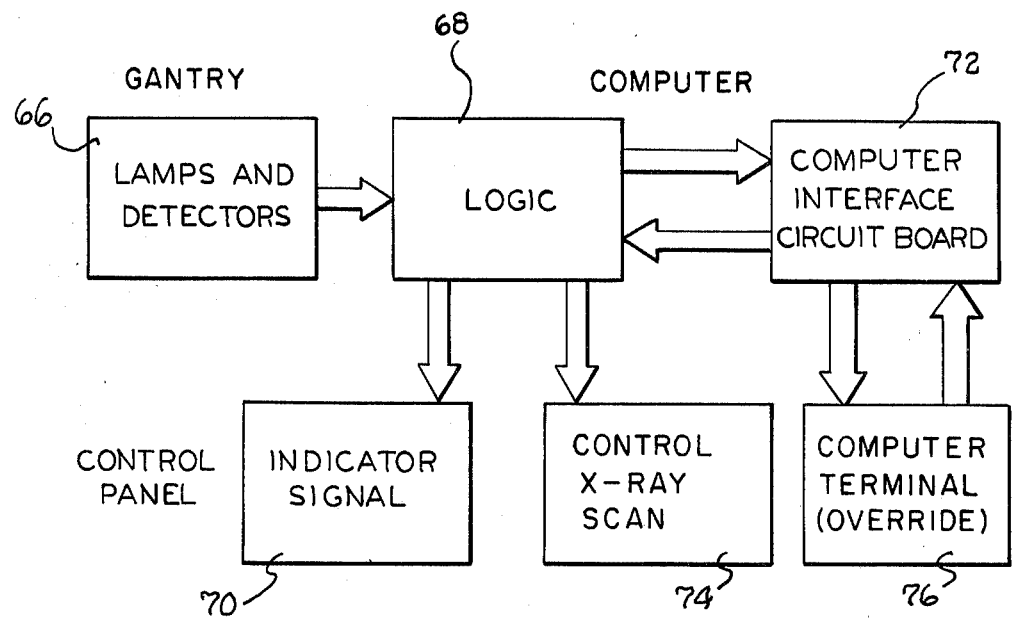
FIG. 5 is a block diagram of the arrangement incorporated into the system.

Referring to FIG. 5 a block diagram describes how the arrangement is incorporated into the tomography system. The patient sensing and indicating arrangement of this invention is designed to inform the computer and the operator if the patient's anatomy under examination is not within the reconstruction circle. The arrangement is incorporated electrically into the control panel, and into the software of the computer of the system. The lamp and detector arrangement is activated prior to advancing the patient into the scanning position. The system in this preferred embodiment is designed so that the patient is translated into the deepest scan, through the sensing arrangement, and then successively sequenced out of the gantry for the additional examining scans. The above sequence allows the entire area of interest to be automatically sensed, and confirmed to be within the reconstruction circle, prior to initiating the first scan and thereby generally precludes interruption of the examination. The arrangement remains activated throughout the examination. The block designated "lamps and detectors" 66, represents the light beam arrangement wired in parallel so that an interruption of any light beam will produce a signal to "logic" circuitry 68. The logic circuitry 68 then initiates and "indicator signal" 70 on the control panel, initiates a signal to the "computer interface board" 72 and initiates a signal to inhibit the "control of x-ray scan" 74. The tomography scanning operation is thereby discontinued at this point and computer interface circuit board 72 prints a "patient oversize" statement at the computer terminal 76. The operator now has two choices, one is to go ahead with the scan and include the patient oversize information for that particular scan file, and two is to abort the current scan and try scanning again. The system will not continue unless an operator responds to the statement with a command such as "override" at computer terminal 76. If the override command is given, circuit board 72 will transmit this statement through the logic to continue operation of the system even though the patient may be extended beyond the reconstruction circle.

Alternatively, the system could be arranged to automatically abort the scanning operation at any time after the detectors sense that a portion of the patient extends beyond the reconstruction circle. An alternative system could also incorporate a simple override or reset switch on the control panel which could reactivate the system and continue with the scanning examination.

As an additional safety feature, once the detectors signal to the logic that a portion of the patient extends beyond the reconstruction circle the logic also initiates a signal to the elevation drives (not shown) of the table and the tilt drive (not shown) for the gantry to prohibit any movement of the table or the gantry as long as the oversize condition exists. This prevents movement of the table or the gantry which might bring the patient in contact with the surface of the cylindrical opening (16) of the gantry.

The arrangement of this invention automatically senses and indicates if a patient extends beyond an image reconstruction circle of a computed tomography system. The arrangement does not interfere with the patient or the scanning operation and is immediately adjacent the scan plane of the system to monitor the size and position over the area of the patient to be examined, immediately prior to initiating the scanning operation. If a portion of the patient is found to extend beyond the reconstruction circle the arrangement cooperates with the software of the system to provide an oversized indication lamp on the control panel and to initiate a statement to the computer terminal which requires an operator response in order to continue the examination.

While specific embodiments of the present invention have been illustrated and described herein, it is realized that modifications and changes will occur to those skilled in the art. It is therefore to be understood that the appended claims are intended to cover all such modifications and changes as fall within the true spirit and scope of the invention.

What is claimed as new and desired to be secured by Letters Patent of the United States is:

1. An arrangement for sensing and indicating if a cross-section of a patient extends beyond an image reconstruction circle during examination by a computed tomography system, said arrangement comprising:
   (a) at least one light emitting source each projecting a light beam adjacent to the patient and along a line which is generally tangent to a cylinder having a diameter and central axis in agreement with said reconstruction circle;
   (b) a corresponding number of photo detectors aligned to receive each said light beam; and
   (c) means for indicating an interruption of any of said light beams between said source and said detector.

2. The arrangement as recited in claim 1 wherein the patient is supported on a translatable horizontally disposed table within the lower sector of said reconstruction circle and said arrangement comprises two said light emitting sources positioned at each side of the patient so as to project generally vertically directed said light beams.

3. The arrangement as recited in claim 2 wherein said table is translatable so that an area of interest of the patient is extended adjacent to said projections of said light beams.

4. The arrangement as recited in claim 3 which further comprises one said light emitting source positioned at one side and above the table so as to project a generally horizontally directed said light beam.

5. An arrangement for sensing and indicating if the cross section of a patient extends beyond a reconstruction circle of a computed tomography system for examining the patient with penetrating radiation such as x-rays, the system including a source of an x-ray beam and a detector disposed about a generally vertical gantry having a generally cylindrical horizontal opening for receiving the patient, and said system including a horizontal patient supporting table which is translatable along the longitudinal axis generally centered within the opening of the gantry wherein the table is displaceable for the purpose of disposing longitudinally successive layers of the patient into the path of the x-ray beam, said patient sensing and indicating arrangement comprising:

(a) at least one light emitting source disposed within said gantry;

(b) each of said light emitting sources projecting a light beam along a line which is generally parallel with the plane of said reconstruction circle and closely adjacent to a cylinder having a diameter and central axis in agreement with said reconstruction circle;

(c) a corresponding number of photo detectors each disposed within said gantry and aligned to receive each said light beam; and (d) means for indicating an interruption of any of said light beams between any of said source and said detector.

6. The arrangement as recited in claim 5 which comprises two said light emitting sources positioned so as to project generally vertically directed said light beams across the opening of said gantry when said gantry is in the initial position.

7. The arrangement as recited in claim 5 which further comprises one said light emitting source positioned so as to project a generally horizontally directed said light beam across the opening when said gantry is in the initial position.

8. The arrangement as recited in claim 5 wherein said indication means comprises a visual signal on a control panel of the system.

9. The arrangement as recited in claim 5 wherein said indication means comprises a message on a control terminal of the system.

10. The arrangement as recited in claim 5 which further comprises means for discontinuing operation until an operator responds to said indication means.

* * * * *